(12) United States Patent
Hoegerle et al.

(10) Patent No.: US 7,740,628 B2
(45) Date of Patent: Jun. 22, 2010

(54) SURGICAL APPLIANCE

(75) Inventors: Roland Alois Hoegerle, Tuttlingen (DE); Martin Machill, Rietheim-Weilheim (DE); Rainer Haeusler, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 1309 days.

(21) Appl. No.: 10/901,021

(22) Filed: Jul. 27, 2004

(65) Prior Publication Data
US 2005/0033275 A1 Feb. 10, 2005

Related U.S. Application Data

(63) Continuation of application No. PCT/EP03/00911, filed on Jan. 30, 2003.

(30) Foreign Application Priority Data
Feb. 19, 2002 (DE) ................................ 102 07 355

(51) Int. Cl.
*A61B 18/04* (2006.01)
(52) U.S. Cl. .................. 606/27; 408/56; 261/8
(58) Field of Classification Search .................. 606/27, 606/80, 176, 180; 318/400.02; 408/56, 241; 261/8; 422/26, 27
See application file for complete search history.

(56) References Cited

U.S. PATENT DOCUMENTS

| | | | | | |
|---|---|---|---|---|---|
| 1,963,543 | A | * | 6/1934 | Linde et al. | 236/20 R |
| 3,120,845 | A | * | 2/1964 | Horner | 606/180 |
| 3,658,053 | A | * | 4/1972 | Fergusson et al. | 600/364 |
| 3,749,456 | A | * | 7/1973 | Whitaker | 384/118 |
| 3,852,697 | A | * | 12/1974 | Snider | 337/348 |
| 4,233,982 | A | * | 11/1980 | Bauer et al. | 604/256 |
| 4,844,719 | A | * | 7/1989 | Toyomoto et al. | 95/52 |
| 5,571,633 | A | | 11/1996 | Hagiuda | |
| 5,611,329 | A | * | 3/1997 | Lamensdorf | 126/263.07 |
| 5,618,409 | A | * | 4/1997 | Kreill | 210/97 |
| 5,967,285 | A | * | 10/1999 | Mohan et al. | 192/103 F |
| 6,059,806 | A | * | 5/2000 | Hoegerle | 606/180 |

FOREIGN PATENT DOCUMENTS

| | | |
|---|---|---|
| DE | 196 07 123 | 8/1997 |
| DE | 199 53 772 | 5/2001 |
| EP | 0 261 260 | 3/1988 |

* cited by examiner

*Primary Examiner*—Todd E Manahan
*Assistant Examiner*—Victor X Nguyen
(74) *Attorney, Agent, or Firm*—Lipsitz & McAllister, LLC

(57) ABSTRACT

In order to improve a surgical appliance comprising a housing having at least one sealed cavity, and a drive unit arranged in the housing, such that the cavity can be sealed in a simple way, and the formation of germs can be reduced or these can be removed in a simple way from the cavity, it is proposed that a fluid connection be provided for forming a flow path into and out of the cavity, and that at least one sealing element be provided for closing the fluid connection to liquid fluids and opening the fluid connection to gaseous fluids.

19 Claims, 4 Drawing Sheets

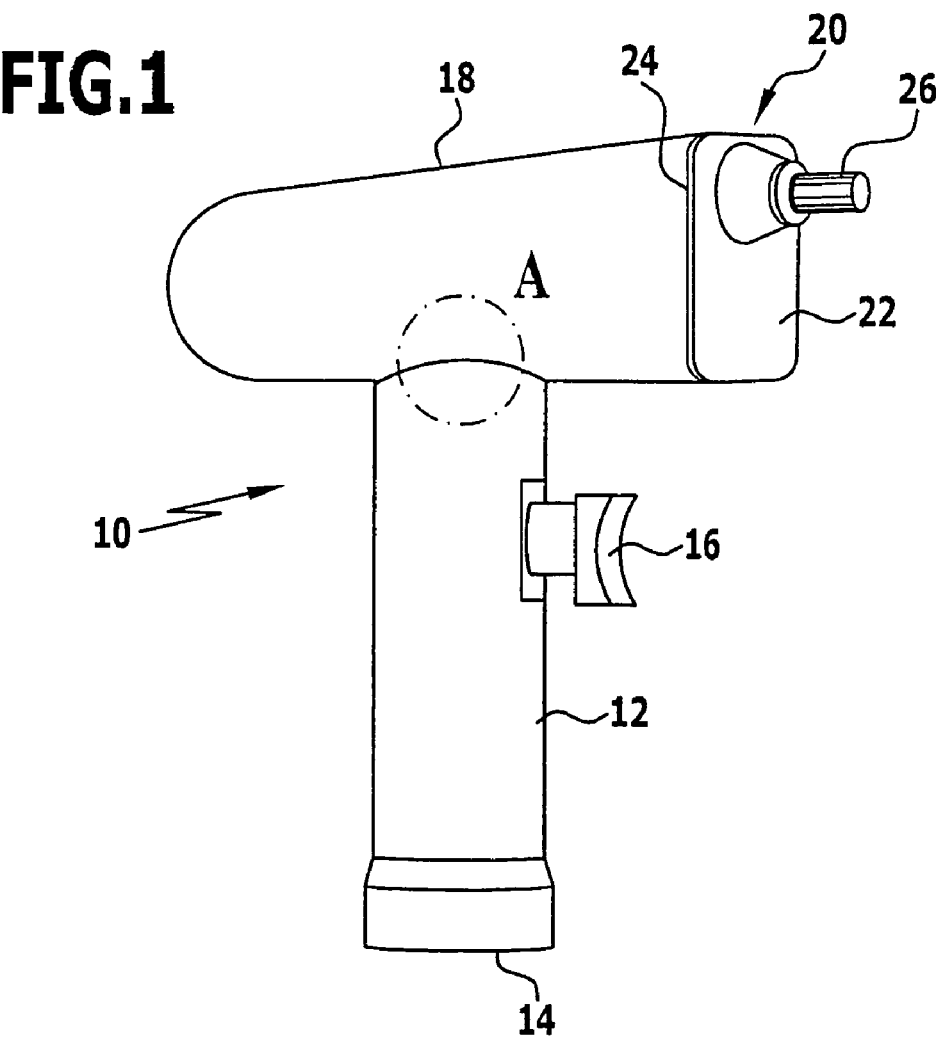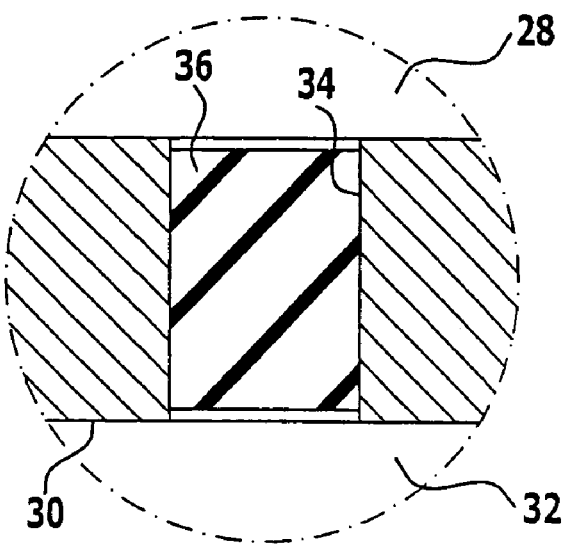

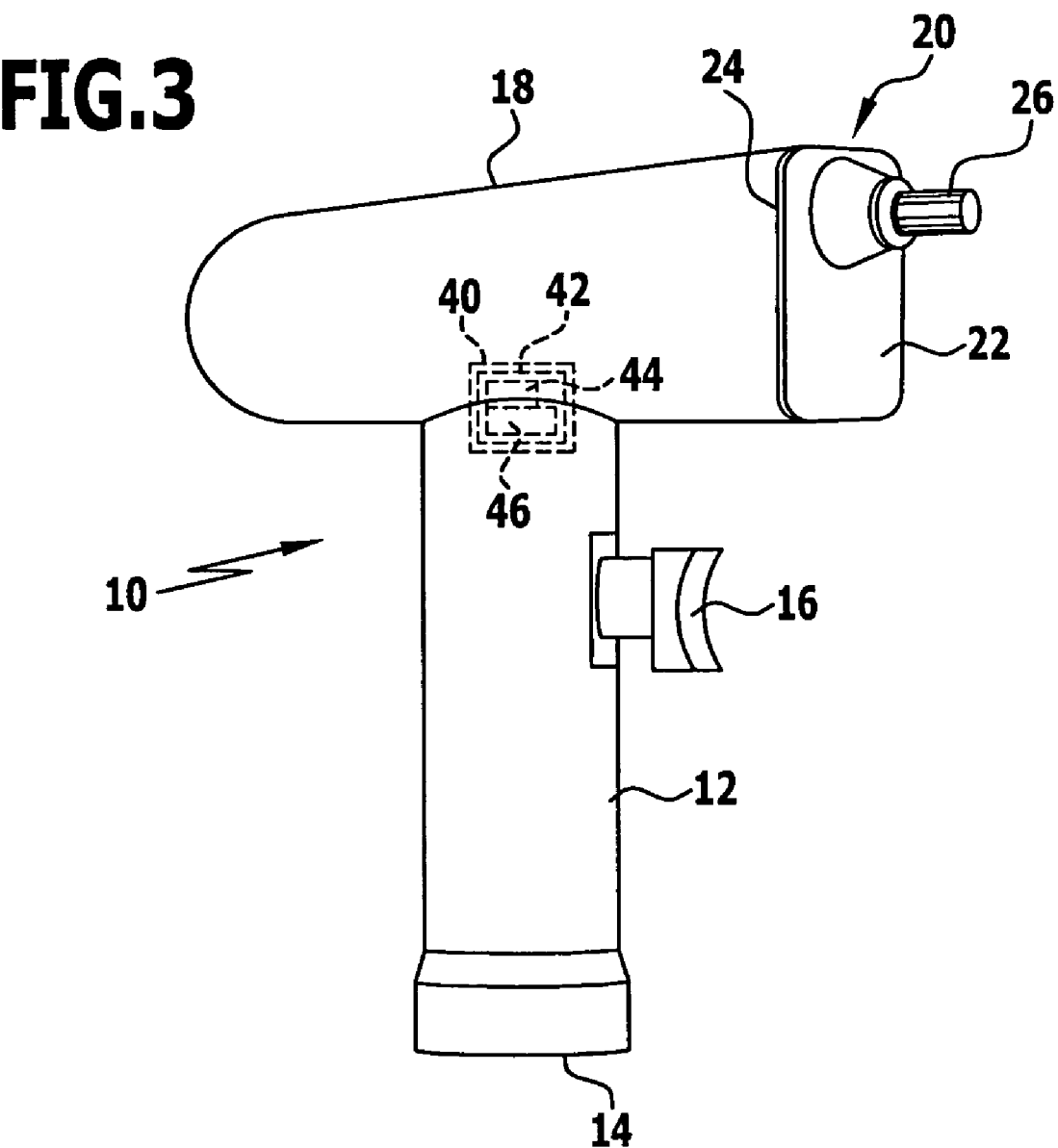

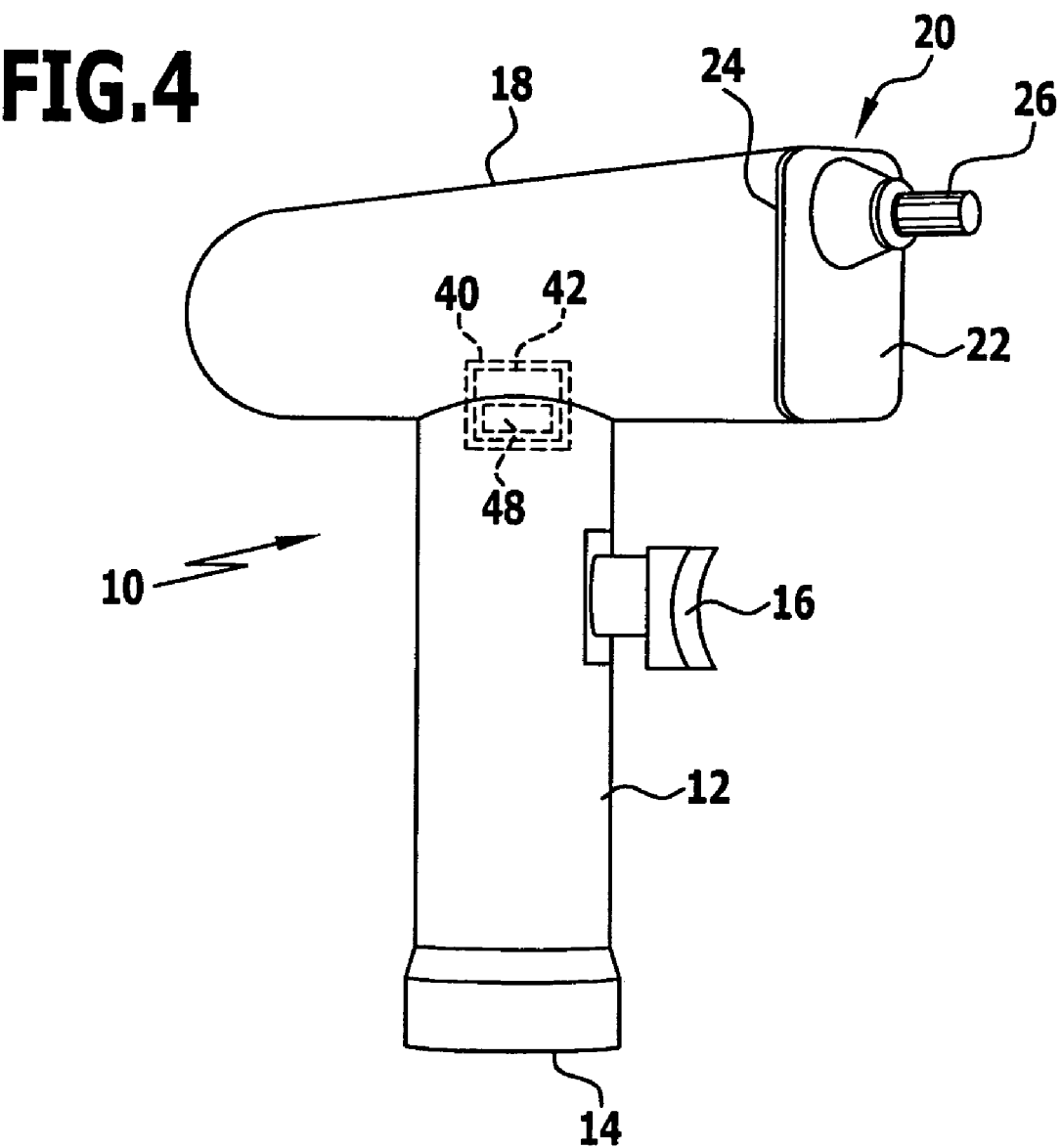

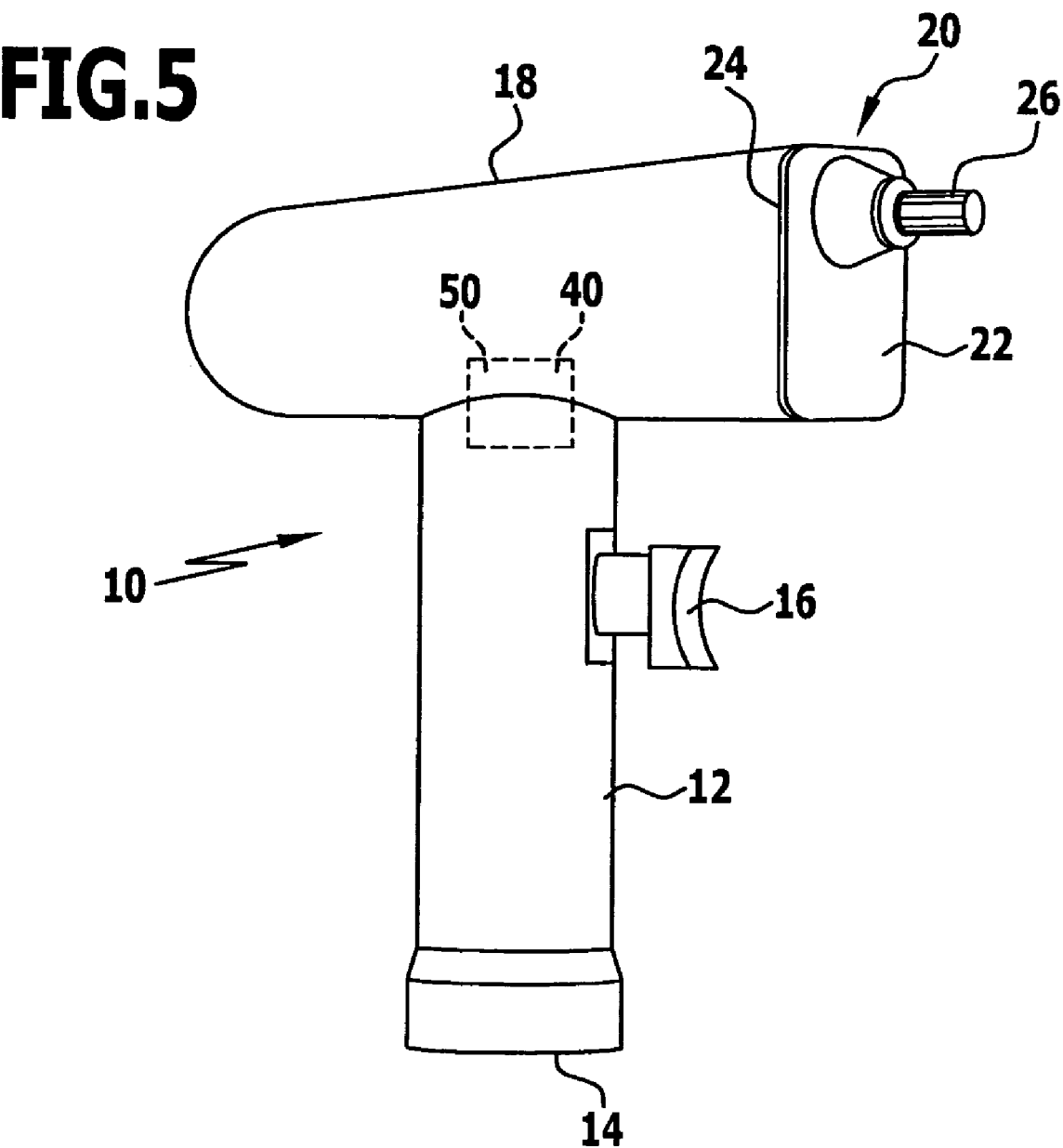

SURGICAL APPLIANCE

The present disclosure relates to the subject matter disclosed in International Application PCT/EP03/00911 of Jan. 30, 2003, which is incorporated herein by reference in its entirety and for all purposes.

BACKGROUND OF THE INVENTION

The invention relates to a surgical appliance comprising a housing having at least one sealed cavity, and a drive unit arranged in the housing.

A surgical appliance of the kind described at the outset is known, for example, from DE 196 07 123 A1.

In the drill disclosed therein, provision is made for a battery to be inserted together with an electronic control unit of an electric motor of the drill into a receptacle provided therefor in the handle of the appliance and to be removed again for sterilization of the appliance. Sterilization of surgical appliances is necessary before they are used at a sterile operating site. However, sterilization at increased temperature, which is usually carried out in the form of a superheated steam treatment, may damage individual components of such appliances, especially electric parts. With the known drill, the battery and the electronic control unit can be protected against harmful sterilization influences, but there is still the problem that during cleaning of the appliances in a washing process with cleaning agent temperatures of above 90° C., sealed-off cavities are only completely tight in an ideal case and can only be permanently sealed to a limited extent.

Furthermore, surgical appliances with drive units always require passages, for example, for a drive shaft, and permanent and complete sealing of these makes high demands on the design and implementation of the sealing connections required therefor. Above all, these seals are also subjected to high mechanical stresses during sterilization as large pressure differences may then occur between inside and outside the sealed cavity. It has proven particularly disadvantageous that small amounts of steam or liquid can always penetrate in an undesired manner into the sealed cavity and can only be removed with difficulty. There is thus the danger that germs from the interior of the sealed cavity may get to a sterile operating site in the reverse direction.

The object of the present invention is, therefore, to improve a surgical appliance of the kind described at the outset such that the cavity can be sealed in a simple way, and the formation of germs can be reduced or these can be removed from the cavity in a simple way.

SUMMARY OF THE INVENTION

This object is accomplished, in accordance with the invention, with a surgical appliance of the kind described at the outset in that a fluid connection is provided for forming a flow path into and out of the cavity, and in that at least one sealing element is provided for closing the fluid connection to liquid fluids and opening the fluid connection to gaseous fluids.

This design enables sterilization of the interior of the cavity in a simple way as gaseous fluids, for example, superheated steam can be passed into the interior of the cavity and removed from it again along the same path by way of the fluid connection. Penetration of cleaning liquid during washing of the appliance, for example, in a washer, via the fluid connection is, on the other hand, prevented. As the surgical appliance can thus be specifically washed from the outside and completely sterilized, i.e., not only on the outside but also on the inside, sealing of the cavity with the expenditure hitherto required is no longer necessary. It is thus possible to make surgical appliances, for example, drills or saws, comprising a drive unit, completely germ-free.

It is expedient for the at least one sealing element to be thermally activatable for opening the fluid connection to gaseous fluids at temperatures which correspond to an activation temperature or have higher values. A flow path is thus only opened, for example, also automatically, for temperatures from the activation temperature upwards. Below this temperature the flow path is closed. It is not possible for liquids or germs to get into or out of the interior of the appliance. Only above the activation temperature, for example, when the appliance is subjected to superheated steam at temperatures above 100° C. during the sterilizing operation, is the fluid connection opened to gaseous fluids.

The activation temperature preferably has a value of at least 120° C. A sterilization prescribed for clinical operation requires temperatures for the sterilization which are above 120° C. If these temperatures are not reached the fluid connection is closed.

It is particularly advantageous for the at least one sealing element to be activatable in a pressure-dependent manner for opening the fluid connection to gaseous fluids at pressure differences between a pressure prevailing inside the cavity and a pressure prevailing outside the cavity, which correspond to an activation difference or have higher values. Any kind of fluid is thereby prevented from penetrating into the interior of the cavity if the activation pressure difference lies below a certain value. The fluid connection can thus also be opened or closed automatically for sterilizing the appliance, for example, in dependence upon the process conditions during the sterilizing operation. It can thereby be ensured that gaseous fluids, for example, superheated steam will only be able to enter the interior of the cavity under certain pressure conditions.

The activation pressure difference is preferably at least 100 hPas. The at least one sealing element is thereby prevented from being unintentionally opened with the usual occurrence of small pressure fluctuations and resulting small pressure differences between inside and outside the cavity.

A particularly simple construction is obtained when the at least one sealing element comprises a membrane and when the membrane is permeable to gaseous fluids and impermeable to liquid fluids. In this way, the appliance can be acted upon in a cleaning apparatus, for example, a washer, with hot or boiling water, without the water or any cleaning and disinfecting agents contained therein being able to penetrate into and contaminate the interior of the cavity. At the same time it is, however, possible for gaseous fluids, for example, superheated steam to pass into the interior of the cavity in order to sterilize it. Liquid forming in the cavity, for example, by way of condensation can, in turn, be removed from the cavity through the membrane by heating-up of the appliance and evaporation of the liquid. A sterile and dry atmosphere can thus be created in the interior. At the same time, a pressure equalization is possible via the at least one sealing element in the form of a membrane, which reduces or totally eliminates stresses at housing parts or seals.

The at least one sealing element is preferably made of a sintered material. Sintered materials can be manufactured in a simple way and specifically adjusted in their permeability to certain molecules. For example, a membrane may also be made of a sintered material.

Provision may be made in a further preferred embodiment of the invention for the at least one sealing element to be made of a ceramic material. Ceramics, which may likewise be sintered, can also be produced in a desired manner with respect to their permeability to fluids.

A particularly cost-effective and reliable design of the at least one sealing element is obtained when these are made of a porous or foamed plastic material. For example, membranes with good breathing properties, such as the membranes sold under the brand names Goretex® and Sympatex® can be used as sealing element.

It is advantageous for the at least one sealing element to comprise a mechanically actuatable valve assembly with at least one valve. This opens up the possibility of opening or closing the fluid connection manually in a specific manner. However, it is also conceivable for the mechanically actuatable valve assembly to be automatically opened or closed as a result of certain prevailing pressure differences or in dependence upon prevailing temperatures.

A particularly simple construction of the valve assembly is obtained when the at least one valve is a diaphragm valve.

To control the sterilizing operation in a more specific way, it is expedient for the valve assembly to comprise an intake valve and a discharge valve. The treating of the interior of the cavity with superheated steam can thus be carried out at, for example, other temperatures or pressure differences than the drying and/or dehumidifying of the cavity.

The intake valve preferably has a higher activation pressure difference than the discharge valve. In this way, a fluid can only enter the interior of the cavity under specific conditions, for example, during sterilization.

The design of the valve assembly is particularly simple when the valve comprises a ball thrust member.

It is expedient for the at least one valve to be actuatable by a bimetal or to be a bimetal. It is thus possible to form in a simple way a valve actuatable in a temperature-dependent manner, which, for example, opens the fluid connection when an activation temperature is reached and exceeded.

It is particularly simple to produce a fluid connection when this comprises a bore.

To make undesired penetration of the fluids into the interior of the cavity more difficult, provision is made for the fluid connection to comprise a labyrinth-type channel.

In principle, any surgical appliance comprising a drive unit may be provided with a fluid connection designed in accordance with the invention. However, the surgical appliance is preferably a surgical drill or a surgical saw.

The following description of a preferred embodiment of the invention serves in conjunction with the drawings to explain the invention in greater detail.

BRIEF DESCRIPTION OF THE DRAWINGS

FIG. 1 shows a perspective view of a surgical hand drill;
FIG. 2 shows an enlarged view of area A in FIG. 1;
FIG. 3 shows a perspective view of a further embodiment of a surgical appliance;
FIG. 4 shows a perspective view of a further embodiment of a surgical appliance; and
FIG. 5 shows a perspective view of a further embodiment of a surgical appliance.

DETAILED DESCRIPTION OF THE INVENTION

FIG. 1 shows a surgical hand drill generally designated by reference numeral 10, which is operated by a battery or an accumulator, which may be inserted into a battery receptacle 32 of a hollow handle 12 of the hand drill 10. The hollow handle 12 is closable by a cover 14. A switch knob 16 interacting with the battery and an electronic control unit connected to the battery is arranged so as to be movable transversely to a longitudinal direction of the handle 12 for operating the hand drill 10.

An elongate motor housing 18 is arranged transversely to the handle 12, and one end face 20 thereof is closed off by a housing cover 22. A seal 24 is inserted between the housing cover 22 and the motor housing 18. A shaft 26 driven by a motor, not illustrated, arranged in the motor housing 18 extends out through the housing cover 22. The shaft 26 may be connected to drilling tools.

The motor housing 18 encloses a completely sealed-off cavity 28. A bore 34 passes through a dividing wall 30 which separates the cavity 28 from the battery receptacle 32. The bore 34 is closed by a membrane 36 which is permeable to gaseous fluids, but closes the bore 34 off completely to liquid fluids. The membrane 36 may be made of a ceramic material, a porous or foamed plastic material or a sintered material, for example, a metal.

Alternatively, it is also conceivable to insert a mechanically operating valve, for example, a ball thrust member or a bimetal into the bore 34. A diaphragm valve which closes the bore 34 is also conceivable. A labyrinth-type channel closable by the sealing element described in conjunction with the bore 34 and inserted therein could be provided as an alternative to the bore 34.

Alternative embodiments of surgical appliances are shown in FIGS. 3 through 5.

The surgical appliance shown in FIG. 3 has a sealing element 40 which comprises a mechanically actuatable valve assembly 42 with at least one valve. Preferably, the valve assembly comprises an intake valve 44 and a discharge valve 46. In an alternative embodiment shown in FIG. 4, the at least one valve comprises a ball thrust member 48.

The surgical appliance shown in FIG. 5 has a sealing element 40 which is a diaphragm valve 50.

The invention claimed is:

1. Surgical appliance comprising:
a housing having at least one sealed cavity,
a drive unit arranged in the housing,
a fluid connection for formation of a flow path into and out of the cavity, and
at least one thermally activatable sealing element adapted to close the fluid connection to liquid fluids and open the fluid connection to gaseous fluids;
wherein:
the surgical appliance comprises a tool used in surgery; and
the at least one thermally activatable sealing element adapted to automatically open the fluid connection to said gaseous fluids at temperatures which equal or exceed an activation temperature.

2. Surgical appliance in accordance with claim 1, wherein the at least one sealing element is activatable in a pressure-dependent manner for opening the fluid connection to said gaseous fluids at pressure differences between a pressure prevailing inside the cavity and a pressure prevailing outside the cavity, which correspond to an activation pressure difference or have higher values.

3. Surgical appliance in accordance with claim 2, wherein the activation pressure difference is at least 100 hPas.

4. Surgical appliance in accordance with claim 3, wherein the fluid connection comprises a labyrinth-type channel.

5. Surgical appliance in accordance with claim 1, wherein the at least one sealing element is made of a sintered material.

6. Surgical appliance in accordance with claim 1, wherein the at least one sealing element is made of a ceramic material.

7. Surgical appliance in accordance with claim 1, wherein the at least one sealing element is made of a porous or foamed plastic material.

8. Surgical appliance in accordance with claim 1, wherein the at least one sealing element comprises a mechanically actuatable valve assembly with at least one valve adapted to close the fluid connection to said liquid fluids and open the fluid connection to said gaseous fluids.

9. Surgical appliance in accordance with claim 8, wherein the at least one valve is a diaphragm valve adapted to close the fluid connection to said liquid fluids and open the fluid connection to said gaseous fluids.

10. Surgical appliance in accordance with claim 8, wherein the valve assembly comprises an intake valve and a discharge valve adapted to close the fluid connection to said liquid fluids and open the fluid connection to said gaseous fluids.

11. Surgical appliance in accordance with claim 10, wherein the intake valve has a higher activation pressure difference than the discharge valve adapted to allow a fluid to enter the interior of the cavity only under specific conditions.

12. Surgical appliance in accordance with claim 8, wherein the at least one valve comprises a ball thrust member adapted to close the fluid connection to said liquid fluids and open the fluid connection to said gaseous fluids.

13. Surgical appliance in accordance with claim 8, wherein the at least one valve is actuatable by a bimetal or is a bimetal adapted to close the fluid connection to said liquid fluids and open the fluid connection to said gaseous fluids in a temperature dependent manner.

14. Surgical appliance in accordance with claim 1, wherein the fluid connection comprises a bore.

15. Surgical appliance in accordance with claim 1, wherein the tool is a surgical drill or a surgical saw.

16. Surgical appliance comprising:
a housing having at least one sealed cavity,
a drive unit arranged in the housing,
a fluid connection for formation of a flow path into and out of the cavity, and
a gas-permeable membrane which is impermeable to liquid fluids for sealing the fluid connection against liquid fluids while permitting the flow of superheated steam into and out of the cavity.

17. Surgical appliance in accordance with claim 16, wherein the gas-permeable membrane is thermally activatable for opening the fluid connection to said gaseous fluids at temperatures which equal or exceed an activation temperature.

18. Surgical appliance in accordance with claim 17, wherein the activation temperature has a value of at least 120° Celsius.

19. Surgical tool, comprising:
a housing having at least one sealed cavity,
a drive unit arranged in the housing,
a fluid connection for formation of a flow path into and out of the cavity, and
at least one thermally activatable sealing element adapted to close the fluid connection to liquid fluids and open the fluid connection to gaseous fluids comprising superheated steam;
wherein the at least one thermally activatable sealing element opens the fluid connection to said gaseous fluids at temperatures which equal or exceed an activation temperature.

* * * * *